United States Patent
Horgan

(10) Patent No.: US 7,117,607 B2
(45) Date of Patent: Oct. 10, 2006

(54) ELECTRONIC INCLINOMETER

(76) Inventor: David Robert Horgan, 8 Old Farm Rd., Wayland, MA (US) 01778

( * ) Notice: Subject to any disclaimer, the term of this patent is extended or adjusted under 35 U.S.C. 154(b) by 0 days.

(21) Appl. No.: 10/900,575

(22) Filed: Jul. 28, 2004

(65) Prior Publication Data

US 2006/0021240 A1 Feb. 2, 2006

(51) Int. Cl.
*G01C 9/06* (2006.01)
(52) U.S. Cl. ............... 33/366.11; 33/512; 702/154
(58) Field of Classification Search ........... 33/1 N, 33/365, 366.11, 366.27, 512; 702/150, 151
See application file for complete search history.

(56) References Cited

U.S. PATENT DOCUMENTS

| | | | |
|---|---|---|---|
| 4,102,055 A | 7/1978 | Volk, Jr. ............... 33/345 |
| 4,348,562 A | 9/1982 | Florin et al. |
| 5,181,525 A * | 1/1993 | Bunnell ............... 600/594 |
| 5,832,422 A * | 11/1998 | Wiedenhoefer ........... 33/1 N |
| 6,353,950 B1 | 3/2002 | Bartlett et al. ............ 5/617 |
| 6,611,783 B1* | 8/2003 | Kelly et al. ............ 702/150 |
| 6,640,246 B1* | 10/2003 | Gary et al. ............ 709/223 |
| 6,892,405 B1* | 5/2005 | Dimitriu et al. ............ 5/615 |
| 2003/0197679 A1* | 10/2003 | Ali et al. ............... 345/158 |
| 2004/0010390 A1* | 1/2004 | Kelly et al. ............ 705/150 |
| 2004/0046668 A1 | 3/2004 | Smith et al. |
| 2004/0103475 A1 | 6/2004 | Ogawa et al. |
| 2004/0127807 A1* | 7/2004 | Hatlesad et al. ............ 600/529 |
| 2005/0083207 A1* | 4/2005 | Smith et al. ............ 340/668 |
| 2005/0097675 A1* | 5/2005 | Borders et al. ............ 5/713 |

OTHER PUBLICATIONS

Acumar Digital Inclinometer Suite *at* http://www.acumar.com (last visited Jul. 26, 2004).
Memsic Inclination Sensing with Thermal Accelerometers #AN-00MX-007 *at* http://www.memsic.com.
Memsic Inclination Sensing of Moving Vehicle #AN-00MX-012 *at* http://www.memsic.com.
International Search Report for International Application No. PCT/US2005/026656, mailed Dec. 9, 2005 (3 pages).
Written Opinion of the International Searching Authority for International Application No. PCT/US2005/026656, mailed Dec. 9, 2005 (5 pages).

* cited by examiner

*Primary Examiner*—G. Bradley Bennett
(74) *Attorney, Agent, or Firm*—Kirkpatrick & Lockhart Nicholson Graham LLP

(57) ABSTRACT

An apparatus used for notifying a user of a patient's upper body physical orientation. The apparatus uses an inclinometer that is attached in the region of the patient's upper body to measure the physical orientation of the patient's upper body, which is then transmitted to a display. In one embodiment, the display can be set to display a plurality of alarm conditions. In other embodiments the patient upper body orientation information is transmitted to a processor and then to the nurses' station or to a ventilator. The invention also relates to a method for measuring the physical orientation of a patient, using such an apparatus.

20 Claims, 5 Drawing Sheets

ELECTRONIC INCLINOMETER

FIELD OF THE INVENTION

This invention relates generally to medical devices to prevent pneumonia and other complications in bedridden patients and specifically devices to warn clinicians about improper patient upper body physical orientation.

BACKGROUND OF THE INVENTION

Hospitalized bedridden patients are at a high risk of developing pneumonia, choking on food or medicines or developing bed sores. These risks can be lowered by closely monitoring the orientation of the patient's upper body. For example, patients on ventilators are especially vulnerable to developing severe pneumonia. Numerous studies have shown that such cases of pneumonia, known as ventilator-associated pneumonia, often can be prevented by elevating the upper body of the patient relative to the lower body.

While elevating the head of the bed is simple in principle, it is elusive in practice. This is because there are many reasons to lower the patient's head during the course of patient care. Some of these reasons include transport, bathing, or bedside medical procedures. Frequently, after the patient's upper body has been lowered for another reason, the clinical care giver forgets to place the patient back in the upper body elevated position. As a result, it is very common for adequate head elevation not to be maintained properly over the course of the bedridden period.

The present invention helps to avoid this problem.

SUMMARY OF THE INVENTION

This invention relates to an apparatus for notifying a caregiver of a the upper body physical orientation of the patient. In one embodiment, the apparatus includes an inclinometer that is attached in the region of the patient's upper body to measure the patient's upper body physical orientation. That measurement is then displayed on a display device to indicate prominently the orientation of the patient's upper body. In one embodiment the inclinometer is attached to the bed frame. In another embodiment it is attached to the patient. In one embodiment, the display is green when the patient's upper body orientation is favorable and red when the orientation is unfavorable. In another embodiment, the device includes a processor that allows the caregiver to input a plurality of alarm conditions thereby alerting the caregiver of an unfavorable patient upper body position. In one embodiment, the apparatus sends patient's upper body orientation information to the nurse's station. In still another embodiment the apparatus sends the patient's upper body orientation information to a ventilator connected to the patient.

This application also relates to a method for measuring the physical orientation of a patient's upper body. In one embodiment, the patient's upper body physical orientation is measured using an inclinometer and then displayed on a display unit. In another embodiment the display unit is backlit green to indicate correct patient's upper body orientation. In another embodiment the patient's upper body orientation information is transmitted to a processor. In still another embodiment, the apparatus transmits the patient's upper body orientation information to a nurses' station. In another embodiment the apparatus transmits the patient upper body orientation information to a ventilator connected to the patient. In another embodiment the processor is programmed to alert the caregiver of a plurality of an alarm conditions.

BRIEF DESCRIPTION OF DRAWINGS

These and other aspects of this invention will be readily apparent from the detailed description below and the appended drawings, which are meant to illustrate and not to limit the invention, and in which.

DETAILED DESCRIPTION OF THE PREFERRED EMBODIMENT

Figure 1:
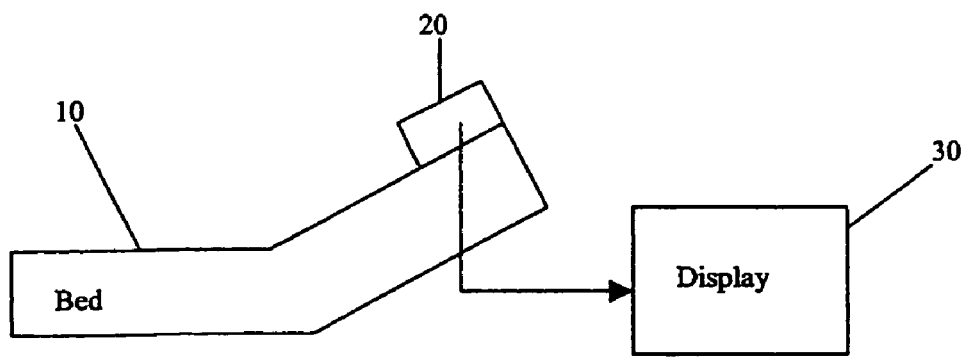
FIG. 1 depicts an embodiment of the invention.

In brief overview, FIG. 1 shows one embodiment of the invention. An inclinometer 20 is attached in the region of the patient's upper body. The inclinometer 20 measures the patient's physical orientation of the patient's upper body. The inclinometer 20 sends the resulting measurement to the display screen 30.

Bed angle is especially important for bedridden patients for a variety of reasons. For example, for a patient connected to a ventilator, ventilator associated pneumonia can be reduced by maintaining the upper body of the ventilated patient at an angle of thirty degrees or greater. In one embodiment, the apparatus is programmed to alert the hospital staff when the upper body of a patient on the ventilator is below 30 degrees. In one embodiment, the display color is solid green when the patient's upper body is 30 degrees or greater. When the upper body is under 30 degrees, the display is colored blinking red. An additional embodiment uses sound as the alarm mechanism, such as a bell, horn or tone. In another embodiment, the words "Ventilated Patients Beds Must be Elevated to at Least 30 Degrees" are printed by the display.

The invention is also useful for patients who have recently had strokes, are weak or have a high risk of inhaling their food and drink. Any of these situations can lead to a possibly fatal event of the patient choking on food, saliva or other bodily fluids or substances The apparatus can be set to aspiration precautions which instructs the caregiver to elevate the head of the bed to 45 or 60 degrees when the patient is eating or drinking.

Additionally, the patient can develop pressure sores on the buttocks and lower back when the angle is much higher than 30–35 degrees. Therefore, in another embodiment, the apparatus can be programmed to display an alarm when the patient's upper body has been above 35 degrees in excess of the pre-programmed time. In another embodiment of the invention, the display contains selection buttons: one for a mobile patient which has no limit for time above 35 degrees, and another for an immobilized patient which is set to a maximum time of 15 minutes above 35 degrees or other predetermined angle.

Figure 2:
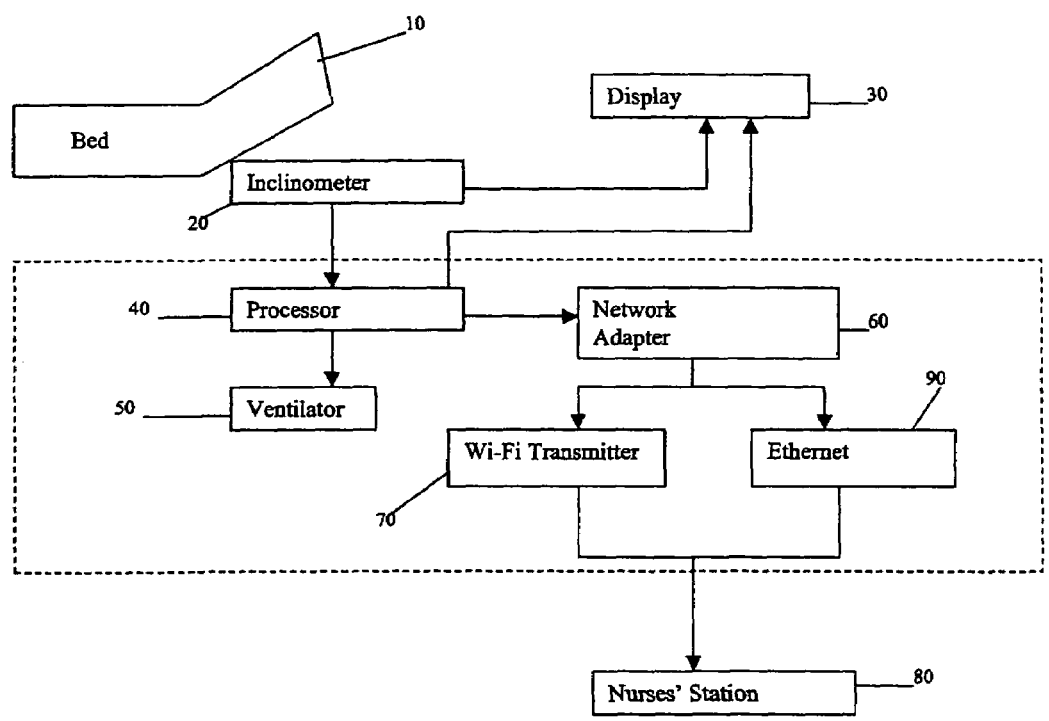
FIG. 2 depicts another embodiment of the invention.

FIG. 2 depicts another embodiment of the invention. In this embodiment, the inclinometer 20 is attached to the region of the patient's bed 10 corresponding to the patient's upper body. The display 30 alerts the user to the orientation of the patient's upper body and warns if the orientation is incorrect. In one embodiment, the inclinometer 20 is a solid state detector that produces an analog signal, which is used to drive the display. The display 30 is in one embodiment a LCD screen, a set of lights, an off or off display or any number of forms that may be used to alert the user. In another embodiment, the user can continuously view the display screen to offer the user a constant reminder regarding the patient's upper body orientation.

In another embodiment shown phantom, the inclinometer 20, a solid state detector, has an analog voltage output 22 which is connected to the display and a serial digital output which is connected to a serial port of a processor 40. The processor 40 determines the orientation of the patient and then sends a signal regarding patient orientation to any number of devices. In one embodiment, the output is sent to an input channel of a ventilator 50. In another embodiment of the invention, the processor 40 transmits the patient upper body orientation information to a network adapter 60 and then to a Wi-Fi transmitter 70 or to an Ethernet connection 90, which then relays the orientation information to various other devices and locations. In one such embodiment, the information is relayed to the nurses' station. In another embodiment, the patient orientation information is relayed to a personal digital assistant. In still another embodiment, the patient orientation information is relayed to a cell phone. In yet another embodiment, the patient orientation information can be relayed to the nurse call system, enabling the processor to call the nurse to the patient's room. In another embodiment, the processor can be programmed to alert the user at different settings or alarm conditions.

Figure 3:
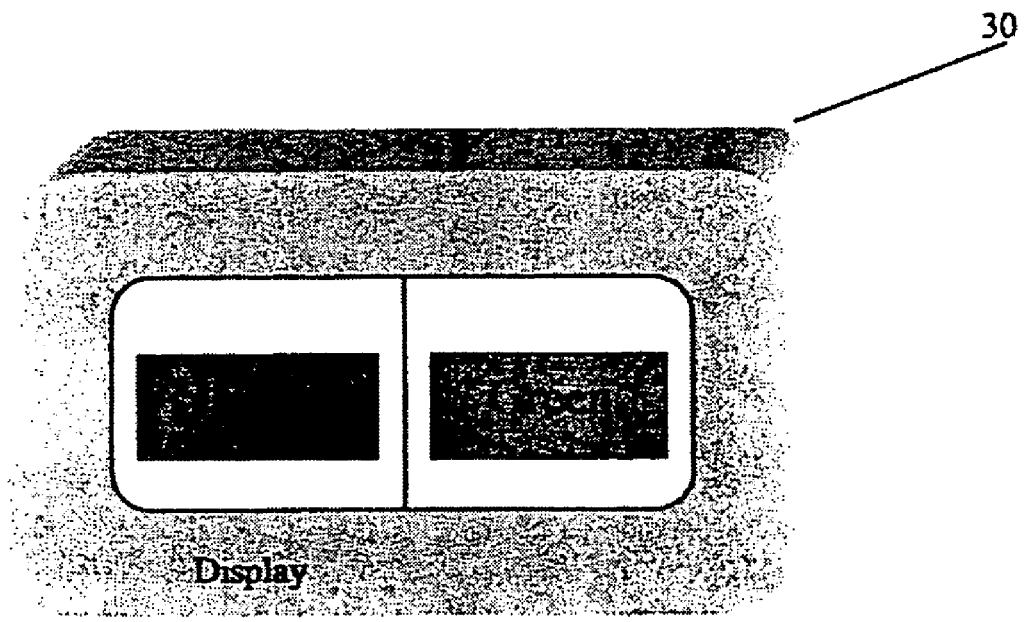
FIG. 3 depicts an embodiment of the display device.

In another embodiment, the inclinometer is attached to the patient's body directly instead of to the bed 10. In the home care setting, the caregiver may use pillows rather than a mechanical bed to elevate the patient's upper body. Having the inclinometer attached to the patient's body, the caregiver can maintain correct head elevation without the use of a mechanical bed FIG. 3 depicts an alternate embodiment of the invention where the display 30 has no corners, so that the display 30 will be less likely to catch itself on IV infusion lines or other various lines connected to the patient. In one embodiment, the display 30 offers a continuous notification to the user of patient's physical orientation. Inclinometer 20 outputs an analog signal which can be used to drive the display 30. The display 30 can be an LCD screen, a set of on/off lights or any number of different displays as known to one skilled in the art. In another embodiment of the invention, the display can be all analog to show patient upper body orientation or minimum upper body orientation and can trigger the appropriate light when the upper body orientation meets any one of the other preset alarm conditions.

Figure 4:
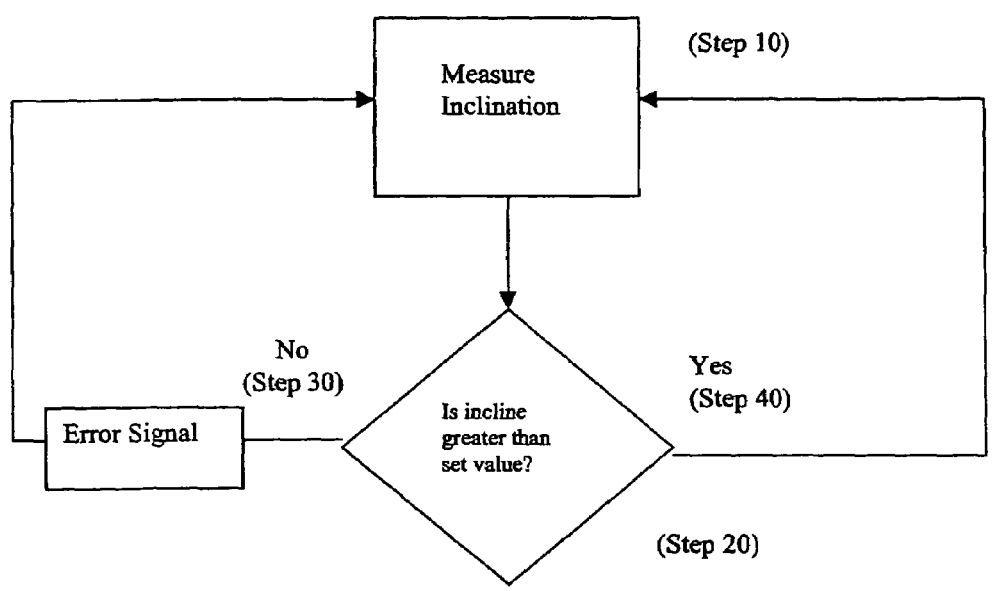
FIG. 4 depicts an embodiment of the method of the invention.

FIG. 4 depicts the alarm method. In one embodiment, the processor 40 reads (Step 10) the patient upper body orientation value from the inclinometer 20. The processor 40 then checks to see if the patient upper body orientation value is above or below the set value for the alarm condition (Step 20). If the alarm condition is met (Step 30), the processor sends a signal to alarm mechanism. If the alarm condition is not met (Step 40), the signal loops back to the inclinometer 20 to read in another patient upper body orientation value. In various embodiments, the alarm can be verbal, audio, visual, a display change, a light, or a warning to another set of devices.

Figure 5:
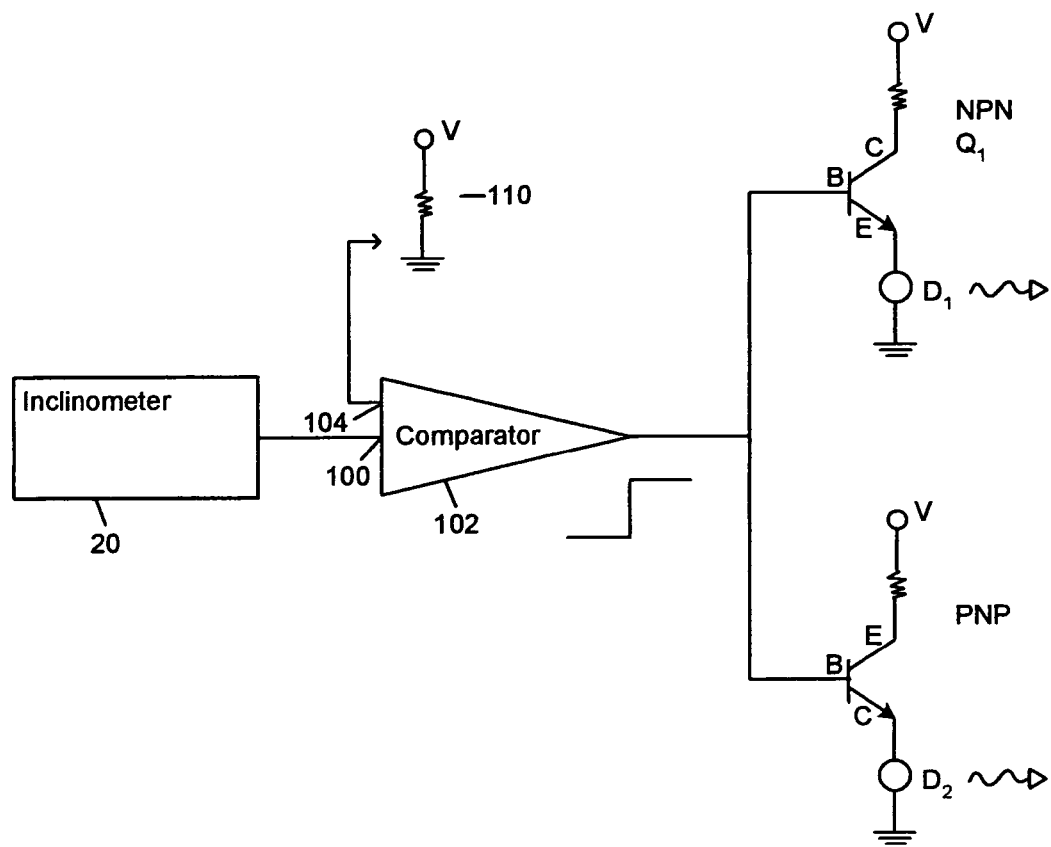
FIG. 5 depicts an embodiment of a circuit of the invention.

FIG. 5 depicts an embodiment of a circuit of the invention utilizing the analog voltage output from the inclinometer 20. The inclinometer 20 outputs a voltage, which is sent to one input of an comparator 102. The other input 104 of the comparator 102 is connected to a potentiometer 110. The comparator 100 then compares the voltage from the inclinometer 20 to a voltage preset by the user using the potentiometer 110. The user presets the voltage applied to the input of the comparator 102 using a dial, button or any of the numerous ways to set a voltage. The comparator 102 then either outputs a high or low signal depending upon the comparison of the desired inclination and the actual inclination of the patient's upper body. The high signal generated by the comparator when the inclinometer 20 voltage output is equal or greater than the preset value. The low signal corresponds to when the inclinometer 20 output voltage is less than the preset voltage. If the signal is high, a light emitting diode D1 illuminates and if the voltage is low, a light emitting diode D2 illuminates. In one embodiment diode D1 and diode D2 have different colors. Thus, the caregiver can set the voltage to display different colors for different values of the upper body orientation of the patient.

In another embodiment the caregiver can input into the apparatus an angle of inclination of the patient's upper body and the amount of time the patient may be non-detrimentally in that orientation or the amount of time the patient may rest outside of the allowed orientation. When the patient's upper body is at the set orientation or outside the required orientation, a timer starts to run. When the patient is in the set orientation or outside the preferred orientation longer than the amount of time set by the caregiver, the apparatus sends an alarm. Thus, when the angle is changed for a medical reason, the apparatus can record when the patients orientation is not in the desired orientation range and alert the caregiver when the patient is at that orientation for a detrimental amount of time.

It should be appreciated by those skilled in the art, that various omissions, additions, and modifications may be made to the methods and systems described above without departing from the spirit of the invention. All such modifications and changes are intended to fall within the scope of the invention as illustrated by the appended claims.

What is claimed is:

1. An apparatus for notifying a user of the physical orientation of a bedridden patient's upper body comprising:
    an inclinometer for attachment in the region of the patient's upper body; and
    a display unit in electrical communication with said inclinometer wherein said display unit indicates the orientation of the patient's upper body and alerts the caregiver if the orientation falls outside a predetermined range selected for the purpose of inhibiting complications associated with bedridden patients.

2. The apparatus of claim 1 wherein said inclinometer is attached to a bed frame.

3. The apparatus of claim 1 wherein said inclinometer is attached to patient.

4. The apparatus of claim 1 wherein said display unit contains a red and a green colored backlight.

5. The apparatus of claim 4 wherein said red colored backlight blinks to alert the user of incorrect physical orientation of the patient's upper body.

6. The apparatus of claim 1 further comprising a processor in communication with said inclinometer.

7. The apparatus of claim 6 wherein said processor sends patient upper body orientation information to a nurses' station.

8. The apparatus of claim 6 wherein said processor sends patient upper body orientation information to a ventilator.

9. The apparatus of claim 1 wherein said display unit has no corners.

10. The apparatus of claim 6 wherein said processor is programmed by the user to alert the user of a plurality of patient upper body orientation conditions.

11. The apparatus of claim 10 wherein the plurality of patient upper body orientation conditions are selected from the group consisting of a predetermined angle for aspiration precaution, immobility precaution and ventilation precaution.

12. The apparatus of claim 1 wherein the bedridden patient is on mechanical ventilation and the inhibiting complications are associated with the mechanical ventilation.

13. A method for measuring the physical orientation of a bedridden patient's upper body comprising:
measuring physical orientation of patient using an inclinometer;
displaying said inclination with a display unit and;
alerting the caregiver if the orientation falls outside a predetermined range selected for the purpose of inhibiting complications associated with bedridden patients.

14. The method of claim 13 further comprising indicating correct patient orientation with a green backlight on said display unit.

15. The method of claim 13 further comprising transmitting patient upper body orientation information to a processor.

16. The method of claim 15 further comprising transmitting patient upper body orientation information to a nurse's station.

17. The method of claim 15 further comprising transmitting patient upper body orientation information to a ventilator.

18. The method of claim 15 further comprising programming processor to indicate an alarm condition.

19. A method of preventing complications in a bedridden patient comprising alerting a caregiver in the event that the patient's upper body is in an inappropriate orientation for more than a predetermined period of time, wherein the predetermined period of time is greater than zero.

20. An apparatus for preventing complications in a bedridden patient comprising a display that alerts the caregiver in the event that the patient's upper body is in an inappropriate orientation for more than a predetermined period of time, wherein the predetermined period of time is greater than zero.

* * * * *